US 6,746,697 B2

(12) United States Patent
Wolfson

(10) Patent No.: US 6,746,697 B2
(45) Date of Patent: Jun. 8, 2004

(54) **COMPOSITION CONTAINING *HELIOPSIS LONGIPES* ROOT EXTRACT AND ORAL CARRIER**

(75) Inventor: Philip Wolfson, San Anselmo, CA (US)

(73) Assignee: Phytos, Inc., San Anselmo, CA (US)

( * ) Notice: Subject to any disclaimer, the term of this patent is extended or adjusted under 35 U.S.C. 154(b) by 49 days.

(21) Appl. No.: 10/014,909

(22) Filed: Dec. 14, 2001

(65) Prior Publication Data

US 2002/0122778 A1 Sep. 5, 2002

Related U.S. Application Data

(60) Provisional application No. 60/255,410, filed on Dec. 15, 2000.

(51) Int. Cl.[7] .................. A01N 65/00; A61K 35/78
(52) U.S. Cl. ................................ 424/773; 424/725
(58) Field of Search ..................... 424/725; 24/773; 435/410

(56) References Cited

U.S. PATENT DOCUMENTS 6,511,683 B1 * 1/2003 Gahler et al. ............... 424/737

OTHER PUBLICATIONS

Little, Jr., E.L. *Heliopsis longipes, a Mexican insecticidal plant species*, Journal of the Washington Academy of Sciences, vil. 38, No. 8, pp. 269–274 (Aug. 15, 1948).

Molina–Torres, J., et al., *Antimicrobial properties of alkamides present in flavouring plants traditionally used in Mesoamerica: affinin and capsaicin*, Journal of Ethnopharmocology, vol. 64, Iss.3, pp. 241–248 (Mar., 1999).

Gutierrez–Lugo, M.T. et al., *Antimicrobial and cytotoxic activities of some crude drug extracts from Mexican Medicinal Plants*, Phytomedicine, vol. 2 (4), pp. 341–347 (1996).

Romero–R., C.M., et al., *Preliminary Studies of the Antibacterial, Insecticidal and Toxicological Effects of the Chiluan Root (Heliopsis Longipes)*, as translated, Veterinaria Mexico, pp. 151–156 (1989).

Crombie, L. et al., *Amides of Vegetable Origin. Part X. The Stereochemistry and Synthesis of Affinin*, Journal of Chemical Society, pp. 4970–4976 (1963).

Jacobson, M., et al., *Correction of the Source of "Affinin" (N–Isobutyl–2,6,8–Decatrienoamide*, Journal of Organic Chemistry 12, pp. 731–732 (1947) (Emphasis added).

Ogura, M., et al., *Ethnopharmacologic studies. I. Rapid solution to a problem—oral use of Heliopsis longipes—by means of a multidisciplinary approach*, Journal of Ethnopharmacology, 5, pp. 215–219 (1982) (emphasis added).

Ramsewak, R.S., et al., *Bioactive N–isobutylamides from the flower buds of Spilanthes acmella*, Phytochemistry 51, pp. 729–732 (1999).

* cited by examiner

Primary Examiner—David M. Naff
Assistant Examiner—Deborah K. Ware
(74) *Attorney, Agent, or Firm*—Richard C. Litman

(57) ABSTRACT

Compositions based on *Heliopsis longipes* root used orally in treating xerostomia, for dry mouth, increasing salivation, alleviating dry mouth, and in maintaining or improving oral hygiene; as local contact anesthetics; as a cough suppressant, and as an oral sensate-producing desirable sensations in the oropharynx. The herbal composition includes an extract from *Heliopsis longipes* root and an oral carrier for the extract. A suitable amount of extract is from about 0.01 to about 10 weight percent of the overall composition. A variety of compositions include an oral carrier; preferred compositions are: 1) a gum with a solid exterior and a liquid center, both the exterior and center containing an effective amount of the extract composition; 2) a solid gum, 3) lozenges; candies, confections and 4) flavored liquid sprays and drops, and mouthwashes. The invention is further useful as an enhancer and potentiator of flavor.

6 Claims, No Drawings

COMPOSITION CONTAINING *HELIOPSIS LONGIPES* ROOT EXTRACT AND ORAL CARRIER

CROSS-REFERENCE TO RELATED APPLICATION

This application claims the benefit of U.S. Provisional Patent Application Serial No. 60/255,410, filed Dec. 15, 2000.

FIELD OF THE INVENTION

The present invention generally relates to 1) compositions that are used orally in treating the clinical condition known as xerostomia, that increase salivation, alleviate dry mouth and the sensations of dry mouth, and thereby aid in maintaining or improving oral hygiene, and methods of using same; 2) compositions that cause local oral anesthesia by direct contact, thereby alleviating pain and dryness in the oral cavity and pharynx caused by dental conditions, cough, sore throat, radiotherapy, surgery and other treatments that may affect the oral cavity and methods of using same; 3) compositions that may be described as oral sensates, that produce sensations of tingling, numbness, moistness and other sensations, and methods of using same; 4) as a flavor enhancer and potentiator; 5) compositions that may include any potential combinations of effects as described above in 1, 2, 3, and 4, and methods of using same. More particularly, the invention relates to oral compositions that include an herbal extract that address a variety of oral conditions; produce a variety of oral sensations, and methods of using the same.

DESCRIPTION OF RELATED ART

*Heliopsis longipes* S. F. Blake (Asteraceae) is a herbaceous plant species found in Mexico that has been disclosed over fifty years ago as having possible commercial value as a source of insecticide. Little, Jr., E. L., *Heliopsis longipes*, a *Mexican insecticidal plant species*, Journal of the Washington Academy of Sciences, Vol.38, No.8, pp.269–274 (Aug. 15, 1948). More particularly, the roots of *Heliopsis longipes* have been used in Mexico to make local insecticides. Id. This use of the plant was discontinued over four decades ago. While this was one use of *Heliopsis longipes* roots, these roots have been used primarily as a spice or flavoring, as chewing the root causes numbness and tingling in the mouth and tongue and stimulates salivation. Id. These roots were also chewed to relieve toothache. Id. One incident is reported of an adverse effect, when a great, but undisclosed, quantity of these roots was eaten. Id.

Extracts from the roots of *Heliopsis longipes* have been used in a few medical applications. Id. For example, reportedly, such an extract has been used for treating colds and pneumonia, and an alcoholic extract has been tested for use as an anesthetic for tooth extraction. Id. It has also been reported that an extract of these roots possesses antiseptic properties. Molina-Torres, J., et al., *Antimicrobial properties of alkamides present in flavouring plants traditionally used in Mesoamerica*: affinin and capsaicin, Journal of Ethnopharmocology, Vol.64, Iss.3, pp.241–248 (March 1999). A crude methanol extract of *Heliopsis longipes* roots has been described as having the potential to generate anti-infective agents, although this extract reportedly does not show any activity in plate diffusion tests against either *E. coli* (Gram negative bacteria) or *B. subtilis* (Gram positive bacteria). Id.; and Gutierrez-Lugo, M. T., et al., *Antimicrobial and cytotoxic activities of some crude drug extracts from Mexican Medicinal plants*, phytomedicine, Vol.2 (4), pp.341–347 (1996). An ethanol extract of *Heliopsis longipes* roots has been reported as having variable bactericidal effects on *E. coli* and *S. aureus*. Romero-R., C. M., et al., *Preliminary Studies of the Antibacterial, Insecticidal, and Toxicological Effects of Chiluan Root (Heliopsis Longipes)*, as translated, Veterinaria Mexico, pp. 151–156, (1989).

*Heliopsis longipes* roots are known to contain a bioactive alkamide, affinin, identified as N-isobutyl-2E, 6Z, 8E-decatrienamide or N-isobutyldeca-trans-2,cis-6,-trans-8-trienamide. Respectively, Id.; and Crombie, L., et al., *Amides of Vegetable Origin*. part X. The Stereochemistry and Synthesis of Affinin, Journal of Chemical Society, pp.4970–4976 (1963). Affinin has also been identified as N-isobutyl 2,6,8-decatrienoamide in one publication, in another publication, and N-isobutyldodeca-2-trans-6-cis-8-trans-trienamide in another publication. Respectively, Jacobson, M., et al., Correction of the Source of "Affinin" (N-Isobutyl-2,6,8-Decatrienoamide, Journal of Organic Chemistry 12, pp.731–732 (1947) (emphasis added); and Ogura, M., et al., Ethnopharmacologic studies. I. Rapid solution to a problem—oral use of *Heliopsis longipes*—by means of a multidisciplinary approach, Journal of Ethnopharmacology, 5, pp.215–219 (1982) (emphasis added). Purified affinin, prepared from an ethanol extract of *Heliopsis longipes* roots, has been reported as being toxic to certain microorganisms, the toxicity varying for Gram positive and Gram negative bacteria. Molina-Torres, J., et al. An aqueous solution of affinin, prepared from a powder of an ethanol extract of *Heliopsis longipes* roots, has also been reported as having an analgesic effect when administered orally to mice at doses of from 2.5 to 10.0 mg/kg, with severe depression of normal motor activity and two out of five deaths occurring at the highest dose. Ogura, M., et al.

In the one publication where affinin is identified as N-isobutyl-dodeca-2-trans-6-cis-8-trans-trienamide, it was said to be identical with spilanthol, the pungent principle of several Spilanthes species. Ogura, M., et al. However, in the publication of Little, Jr., affinin is said to be similar to spilanthol, which has been isolated from flower heads of a species of Spilanthes. Little, Jr., E. L., at p.270. The flowers and leaves of Spilanthes acmella L. var. oleracea Clarke are reported as having been used as a spice and as a folk medicine for stammering, toothache, stomatitis and throat complaints. Ramsewak, R. S., et al., Bioactive N-isobutylamides from the flower buds of *Spilanthes acmella*, Phytochemistry 51, pp. 729–732 (1999).

SUMMARY OF THE INVENTION

1) The present invention provides compositions based on *Heliopsis longipes* root that are used orally in treating the clinical condition known as xerostomia, or more generally, dry mouth, that increase salivation, alleviating dry mouth and the sensations of dry mouth, and in maintaining or improving oral hygiene, and methods of using the same.

2) The present invention provides compositions based on *Heliopsis longipes* root that may provide some degree of local anesthesia and a sensation of numbness to all or portions of the oropharynx including teeth, gums, lips, tongue, palates, throat, and to the upper respiratory passageways such as the trachea, and bronchi. This provides some degree of relief from pain, dryness, irritation, and inflammation to these regions. There my be an improvement in swallowing that is impaired by illness and drying of the oropharynx. An anti-bacterial and anti-viral affect may also occur with reductions in bacterial and viral counts, and improvement from infections of these anatomical regions.

3) The present invention provides compositions based on *Heliopsis longipes* root that may cause desirable sensations to the same anatomical regions, these sensations consisting of tingling, numbness, moistness, acerbic taste, soothing, and other sensations.

4) The present invention provides compositions that may enhance other flavors, natural and artificial, and combinations of them—by increasing their strength and qualities, and by potentiating flavors in duration and quality.

The herbal composition includes an extract from *Heliopsis longipes* root in an amount sufficient to promote the above goals and an oral carrier for said extract. A suitable amount of the extract is from about 0.01 to about 10 weight percent of the overall composition. preferably, the extract is present in an amount sufficient to provide the above benefits for a prolonged period, i.e., for one minute or more.

A particular advantage of the inventive compositions is that they employ an extract of the *Heliopsis longipes* root, and thus, use a very small amount of the plant itself. This is especially important because the plant is believed to grow in a narrow geographic region, and thus, could become endangered if there were to be overly aggressive harvesting of wild plants. A horticultural project in the region has been started, to farm the plant and avoid any use of plant material from wild sources.

The compositions may be provided in oral formulations such as powders, gels, pastes, tablets, capsules, gums, lozenges, mints, candy, other confectionery materials, aerosols or sprays, fluids, rinses or mouthwashes, dentifrices, such as tooth-powders, tooth-gels, tooth-pastes, and extract-impregnated dental flosses, and the like. A particularly preferred composition is a gum with a solid exterior and a liquid center, wherein both the solid exterior and the liquid center contain an effective amount of the extract composition. A particular advantage of this composition is that the liquid center delivers the extract to the oral cavity quickly thus initiating salivation, while the solid gum delivers additional extract to the oral cavity over a prolonged period, a combination that provides a particularly effective treatment of the oral cavity for maintaining or improving oral hygiene by causing and increasing salivation.

Accordingly, it is a principal object of the invention to provide an herbal composition including an extract from *Heliopsis longipes* root in an amount effective to promote oral hygiene, and/or local anesthesia by contact, and/or a variety of desirable sensations to the same regions and to treat a wide variety of oral disorders, and unpleasant sensations.

It is an object of the invention to provide an herbal composition including an extract from the *Heliopsis longipes* root and an oral carrier in any one of a wide variety of forms; e.g., a powder, a gel, a paste, a tablet, a capsule, an oral film, a mouthwash, a gum, a candy, a confection, a lozenge, a liquid preparation such as a droplet dispenser, or aerosol dispenser, etc.

It is a further object of the invention to provide a method of treating an oral cavity with an herbal composition including a medicinally effective amount of an extract from the *Heliopsis longipes* root.

Further objects and advantages of the present invention will become readily apparent from a review of the following specification and claims.

DETAILED DESCRIPTION OF THE PREFERRED EMBODIMENTS

The present invention provides herbal compositions, which include an extract of *Heliopsis longipes* root, that are formulated for oral use. Herein, the extract of *Heliopsis longipes* root may be called the extract, the *Heliopsis longipes* extract, the *Heliopsis longipes* root extract, and the like, where such terms have the same meaning. The compositions may be provided in oral formulations such as powders, gels, pastes, tablets, capsules, gums, lozenges, aerosols or sprays, fluids, rinses or mouthwashes, dentifrices, such as toothpowders, tooth gels, toothpastes, and extract-impregnated dental flosses, and the like. Regardless of the particular form of the compositions, the compositions include an extract of *Heliopsis longipes* root, as the active component, and a carrier for the extract that is suitable for oral use. When taken or administered orally, the compositions promote increased salivation and improve oral hygiene, and/or cause local anesthesia by contact, and/or a variety of desirable sensations. They may enhance and potentiate other flavorings used in commercial products.

As used herein, oral hygiene refers to acceptable or good health in terms of salivation, moistening of mouth and throat, freshness of breath, dental condition, gum condition, condition of oral mucosa, condition of an oral bio-film, condition of oral bacteria or oral plaque, and/or the like, as well as other specific conditions described herein. Further, as used herein, promoting refers to maintaining a condition of acceptable or good oral hygiene or improving a condition such that acceptable or good hygiene results. As used herein, local anesthesia by contact refers to a numbing and/or diminution of sensation to the tissues, which are in contact with the invention, particularly to a reduction in painful and uncomfortable sensations.

The *Heliopsis longipes* extract may be prepared using standard means or methods, such as by contacting the plant material with an appropriate solvent to prepare a botanical tincture, or by any other conventional means or method, such as by $CO_2$ extraction, freeze-drying, spray-drying, and the like. (See Gennaro AR: Remington: *The Science and Practice of Pharmacy*, Mack Publishing Company, Easton Pa. 1995 and The United States Pharmacopeia 22nd rev, and The National Formulary (NF) 17 ed, USP Convention, Rockville Md., 1990.) The extract is prepared using a root or roots of *Heliopsis longipes* and a solvent, which may be water, such as distilled water, an aqueous solvent, such as water combined with other solvents, an organic solvent, such as hexane and glycerin, or an alcohol, such as ethanol, or any combination thereof. Preferably, an alcohol or a hydro-alcohol solvent is used, and most preferably, ethanol or a combination of ethanol and water is used.

The resulting extract is typically composed of a wet or liquid component that is light brown to golden in color and a dry or solid component, in amounts of about 90.0 to about 99.9 weight percent, such as about 98 weight percent, and about 10 to about 0.01 weight percent, such as about 2 weight percent, respectively, relative to the extract. The composition, including the extract in the wet-dry form just described, may be formulated as a liquid. Alternately, the composition may be formulated as a powder or paste, such as a powder including about 66.6 weight percent extract and 33.4 weight percent carrier on a wet basis; or about 0.01 to about 100 weight percent extract on a dry basis-including the natural product sprayed on itself, such as about 2 to 10 weight percent extract on a dry basis, or in any combination or permutation for either method-wet or dry.

It is important to note here that an affinin standard has been produced, for the first time enabling quantitative assay and standardization of dosage of the active ingredient from batch to batch of products.

According to one aspect of the invention, the extract component of the inventive composition is provided in an amount sufficient to promote oral hygiene, such as from about 0.5 mg to 1000 mg, preferably, from about 10 mg to about 200 mg, and most preferably, from about 10 mg to about 100 mg, per effective dose of the composition. A sufficient amount of the extract component is from about 0.1 to about 10 weight percent relative to the inventive composition. Generally, the liquid, powder, and paste formulations containing such an amount of the extract component are equally efficacious in promoting Treatment of xerostomia, alleviating dry mouth and promoting oral hygiene, causing local anesthesia, and desirable sensations in the oropharynx.

When the inventive composition is placed in a person's mouth, the active extract component generates a characteristic acerbic, lemon- or citron-like taste, and the person will experience a strong, pleasant, tingling sensation in the mouth accompanied by salivation. Salivation is an important element in oral hygiene, as saliva tends to wash the mouth of food, and contaminants; promotes a balanced ecology of the oral cavity including the gums and teeth; and salivation refreshes the mouth. Thus, this property of stimulating the salivary glands makes the inventive composition useful and beneficial for oral and dental hygiene, and dental and oral clinical conditions, these including alleviating xerostomia and the sensations and perception of dry mouth; reducing oral bacteria, reducing dental caries, reducing halitosis, reducing peri-odontitis, reducing oral plaque, and promoting the healing of and alleviation of oral lesions, such as any lesion present in the mouth, a lesion induced by stomatitis, a lesion induced by herpes, and the like. Additionally, because of its local anesthetic effects, the inventive composition may reduce pain, sore throat, and suppress the cough reflex. It may improve swallowing by reducing dryness of the throat through increasing salivation and/or by producing a local anesthetic effect.

By way of example, the inventive composition may be administered to a person diagnosed with xerostomia. Xerostomia may occur as a result of illness, or may occur as a side effect of medications, such as chemotherapeutic agents used for treating cancer, medication for treating Parkinson's disease, medication for treating psychiatric conditions, and the like. According to the present invention, the inventive composition to be administered includes the extract in an amount sufficient to alleviate dry mouth. Preferably, this amount is sufficient to stimulate salivation at a level greater than the level of salivation the person is otherwise able to provide, for a prolonged period. As salivary flow varies from person to person, the amount sufficient to stimulate salivation at the desired level may vary from person to person. Thus, the amount is preferably tailored to the salivary flow condition of a particular person or tailored to an average based on a study of salivary flow conditions for a particular group of people or a statistically relevant group of people. Preferably, the prolonged period of salivary stimulation is about 1 minute or more.

A double blind controlled placebo pilot study of the impact of unflavored gum containing extract of *Heliopsis longipes* on salivation demonstrated a consistent stimulation of salivation of *Heliopsis longipes* above baseline.

Further by way of example, the inventive composition may be useful in reducing oral bacteria, as its *Heliopsis longipes* extract component demonstrates antibiotic efficacy against gram negative and gram positive bacteria, such as those that may be present in an oral cavity, and antibiotic efficacy against other pathogens. An anti-viral effect may also be the result of using the inventive composition.

According to further aspects of the invention, the inventive composition may include the extract in an amount sufficient to reduce dental caries, to reduce halitosis, to reduce periodontitis, to reduce oral plaque, or to alleviate an oral lesion, such as the oral lesions previously described. Generally, for any one of these applications, a suitable amount is from about 0.5 mg to 1000 mg, preferably, from about 5 mg to about 200 mg, and most preferably, from about 10 mg to about 100 mg per effective dose to be administered to a typical adult. As mentioned above, a suitable amount of the extract may be from about 0.01 to about 10 weight percent relative to the composition. These amount may be scaled up or down to arrive at an effective dose to be administered to a particular adult, a child, or elderly person.

In addition to the extract of *Heliopsis longipes* root, the inventive composition also contains an oral carrier. This carrier may be in any of a variety of forms, such as a powder, a gel, a paste, a tablet, a capsule, a gum, a lozenge, an aerosol, and a fluid. For example, the carrier may be a candy, a chewable gum, an oral rinse or a mouthwash, or a dentifrice, such as a toothpowder, a toothgel, a toothpaste, and an extract-impregnated or extract-permeated dental floss. The carrier may include an additive that facilitates its use in an oral cavity, such as a texture-enhancement agent, a chewing-enhancement agent, a thickening agent, and a viscosity-enhancement agent. The carrier may also include flavoring agents, such as sweeteners (sugar, saccharin, sorbitol, or aspartame, etc.), natural or artificial flavors or oils, such as fruit or spice or herbal flavors or oils (cinnamon, clove, or mint oil, etc.), and the like, breath fresheners, such as chlorophyll and/or colorings, such as any suitable conventional coloring agent.

According to one aspect of the invention, the oral carrier has a solid exterior. Suitable carriers include a tablet, a capsule, a gum, and a lozenge. Housed within the solid exterior is an interior material, such as a powder or a fluid, such as a liquid or a gel. When the solid exterior is broken into, such as by incision or biting, or broken down, such as by dissolution or sucking, the interior material is accessible to the oral cavity. Preferably, the interior material is a fluid, as a fluid (particularly a liquid) may facilitate stimulation of the salivary glands under conditions of xerostomia or dry mouth thus resulting in the rinsing of the mouth, causing moistening of the of the solid exterior of the carrier, facilitating chewing of the solid, and the like. At least one of the components, either the solid exterior or the fluid, and preferably both, contain a quantity of the *Heliopsis longipes* root extract. According to this aspect of the invention, a particularly suitable oral carrier is a solid gum that houses a fluid.

When a gum is used as an oral carrier in the inventive composition, it is preferably of a composition sufficient for chewing, and particularly, for chewing for a prolonged period so that the oral cavity and teeth are well exposed to the composition. A suitable prolonged period is 1 minute or more, such as from about 5 minutes to about 2 hours, or preferably, from about 10 minutes to about 1 hour. The gum should have a texture that is palatable and a chewing resistance that is comfortable. Suitable gums include arabic gum, chicle gum, guar gum, natural rubber gum, gum base as used in chewing gums of natural and artificial compositions, and the like, and any combination of these or other gums. The gums may be entirely or partially solid, and coated or uncoated. The gums may be produced in a variety of shapes and forms, such as sticks, chunks, balls, pellets, and hard-shelled or candy-coated gums (such as the hard-shelled gum commercially available under the name "Chicklets").

Regardless of the form of the composition, administration of the composition is that sufficient to provide the composition in the oral cavity for a period sufficient to provide the desired outcome. That is, an effective amount of the active extract component of the composition should be present in the oral cavity for an effective period, and preferably, for a prolonged period, such as 1 minute or more. This may require periodic administration of the composition to the oral cavity, particularly, when prolonged or repeated contact is desirable for treating a particular condition, such as dental caries, oral plaque, periodontal disease or deterioration, and oral lesions.

Regardless of the form of the composition, it may contain a variety of additives, such as preservatives, stabilizing agents, flavoring agents, coloring agents, sweetening agents, such as sugars, sugar substitutes, and sugar-free sweeteners, and the like. Other additives include any of a variety of nutraceuticals and botanical extracts, or any similar additive known to provide a health benefit of its own or to promote a health benefit of the composition or any of its components. possible health additives include chlorophyll, bicarbonate soda, and/or the like. Other possible additives include dispersing agents, surfactants, desensitizing agents, teeth-whitening compounds, active oxygen compounds, fluoride compounds, and/or the like.

According to a particular embodiment of the present invention, the composition is prepared as a liquid that is delivered to the oral cavity as a rinse or a spray. Compositions A and B, described herein, are examples of such liquid compositions. In Table 1, each of the components of Composition A and Composition B are listed along with the approximate amount of each component in weight percent (%) relative to the overall composition. Compositions A and B are sugar-free, as they contain only the sweetener sorbitol. Composition A and B have a "natural" flavor, as no flavor additives are used. Naturally, a flavor additive could be used to impart any of a variety of desired flavors to these compositions.

TABLE 1

Liquid Compositions A and B

| | Component | Composition A Weight Percent (%) | Composition B Weight Percent (%) |
|---|---|---|---|
| 1. | Distilled Water | 48.60 | 47.60 |
| 2. | Glycerin USP 99% 249.00 | 20.00 | 20.00 |
| 3. | Sorbitol Powder | 30.00 | 30.00 |
| 4. | Potassium Sorbate | 0.10 | 0.10 |
| 5. | Sodium Benzoate | 0.10 | 0.10 |
| 6. | Citric Acid Powder | 0.20 | 0.20 |
| 7. | *Heliopsis Longipes* Root Extract (35%) | 1.00 | 2.00 |
| All Components | | 100.00 | 100.00 |

Compositions A and B may be prepared by combining components 1 through 5 in a clean container, such that any solid components are substantially dissolved and the resulting solution is substantially clear. Component 6 is then added to the above combination and substantially dissolved therein. Finally, the active *Heliopsis longipes* extract, Component 7, is added to the combination of components 1 through 6 and substantially dispersed therein. Any appropriate mixing means and methods may be used to facilitate the combining, dissolving, or dispersing of the components to produce the liquid composition. Once prepared, the composition may be delivered to the oral cavity as a rinse or as an aerosol or spray, in any conventional manner. Compositions A and B are particularly effective in alleviating dry mouth.

Other sugar-free compositions, Compositions C and D, are also prepared as a liquid that is delivered to the oral cavity as a rinse or a spray. In Table 2, each of the components of Composition C and Composition D are listed along with the approximate amount of each component in weight percent (%) relative to the overall composition. Compositions C and D have a mint flavor by virtue of the peppermint-flavored component.

TABLE 2

Liquid Compositions C and D

| | Component | Composition C Weight Percent (%) | Composition D Weight Percent (%) |
|---|---|---|---|
| 1. | Distilled Water | 10.95 | 10.82 |
| 2. | Glycerin USP 99% 249.00 | 10.95 | 10.82 |
| 3. | Sorbitol Solution (70/20) | 76.67 | 75.73 |
| 4. | *Heliopsis Longipes* Root Extract (35%) | 1.10 | 2.16 |
| 5. | Peppermint Flavor FFS #3352 | 0.33 | 0.48 |
| All Components | | 100.00 | 100.00 |

Compositions C and D may be prepared by combining components. 1 through 3 in a clean container, such that any solid components are substantially dissolved and the resulting solution is substantially clear. The active *Heliopsis longipes* extract, Component 4, is then added to the combination of components 1 through 3 and substantially dispersed therein. Finally, the flavor component, Component 5, is added to the above combination and substantially dispersed therein. Any appropriate mixing means and methods may be used to facilitate the combining, dissolving, or dispersing of the components to produce the liquid composition. Once prepared, the composition may be delivered to the oral cavity as a rinse or as an aerosol or spray, in any conventional manner. Compositions C and D are particularly effective in alleviating dry mouth.

While Compositions A-D may be prepared as described above, following the orders of addition described above, any other suitable preparation means or method may be used. This holds for the other compositions disclosed herein as well.

According to another particular embodiment of the invention, the composition may be prepared as a liquid-filled gum shell. An amount of *Heliopsis longipes* extract component may be added to the carrier during the making of the gum shell. By way of example, the extract may be provided in a powder form and added to a gum-based carrier. The resultant gum shell may be of any desirable flavor, color, or shape. The gum shell may be filled with a liquid by any conventional means or methods. The liquid may include a liquid formulation, such as any conventional liquid formulation used to fill the center of a gum shell, to which an amount of *Heliopsis longipes* extract has been added.

In the aggregate, the gum and liquid portions of the liquid-filled gum shell contain an aliquot or amount of the *Heliopsis longipes* extract sufficient to promote oral hygiene. Preferably, at least one of the gum and liquid portions, more preferably the liquid portion, contains such an aliquot of the extract. Most preferably, both the gum and liquid portions contain such an aliquot of the extract. When the extract is provided in the liquid portion, and the liquid portion is released to the mouth, salivation is stimulated substantially immediately. This is particularly important to a person experiencing dry mouth, who may have insufficient saliva to moisten the solid gum and thereby initiate its desired activity. When the extract is also provided in solid gum portion, the salivation initiated by the liquid portion is sustained by, and possibly enhanced by, salivation stimulated by the relatively slower release of the extract from the solid gum as it is chewed.

This hybrid, liquid-solid composition may include a number of components, as described below, in various amounts, as described below in ranges of approximate weight percentages (%) relative to the liquid or solid portion of composition. Generally, the solid gum may be composed of the extract and a gum base, sucrose, corn syrup, a coloring agent, and a flavoring agent. Sucrose and corn syrup may be replaced by other sweeteners, such as hydrogenated starch hydrolysate, isomalt, sorbitol, xylitol, and the like, in various ratios. By way of example, the solid gum may be composed of the *Heliopsis longipes* extract (0.1% to 10%); a gum base (10%–90%, preferably 20%–80%); a hydrolyzed protein (1.0%–8.0%, preferably 1.5%–3.0%); a sweetener, such as sucrose (10%–80%, preferably 15%–50%), corn syrup (5%–60%, preferably 10%–30%), hydrogenated starch hydrolysate (5%–60%, preferably 15%–50%), isomalt (10%–80%, preferably 15%–50%), sorbitol (10%–60%, preferably 20%–50%), xylitol (10%–80%, preferably 15%–50%), an artificial sweetener (0.2%–2.0%, preferably 0.5%–1.0%), a natural sweetener, and a sugar-free sweetener; a coloring agent in an amount sufficient to provide a desired color; and a flavor ingredient in an amount sufficient to provide a desired taste. The solid gum may also include a botanical extract, gelatin, glycerin, starch and modified starches, any of which may be in an amount of from about 1.0% to about 7.0%, and preferably from about 1.5% to about 5.0%), and any of which may modify a texture or a chewing property of the solid gum, and/or facilitate the release of the extract from the gum matrix. The texture and physical properties of the finished product may also be affected by the final form of the gum composition, such as whether or not the gum solid is coated or has a hard shell.

The liquid portion of the hybrid composition, or liquid center, may be composed of a number of components, as described below, in various amounts, as described below in ranges of approximate weight percentages (%) relative to the liquid or solid portion of composition. By way of example, the solid gum may be composed of the *Heliopsis longipes* extract (0.1% to 10%); glycerin (10%–80%, preferably 15%–45%); a sweetener, such as sucrose (5%–40% preferably 10%–30%), corn syrup (10%–860%, preferably 15%–50%), a hydrogenated starch hydrolysate (5%–60%, preferably 10%–50%), isomalt (10%–30%, preferably 15%–25%), sorbitol (5%–60% preferably 10%–40%), xylitol (1%–10%, preferably 5%–8%, an artificial sweetener (0.2%–2.0%, preferably 0.5%–1.0%), a natural sweetener, and a sugar-free sweetener; a coloring agent in an amount sufficient to provide a desired color; and a flavor ingredient in an amount sufficient to provide a desired taste. The liquid center may also include a botanical extract, a modified starch, a natural gum, and a thickening agent, any of which may be in an amount from about 0.5% to about 5.0%, and preferably from about 1.0% to about 3.0%), and any of which may stabilize the viscosity of the liquid center.

The solid gum of the hybrid composition may be prepared by pre-warming a gum kettle to 100° C., adding small pieces of a gum base to the kettle and letting the pieces melt while stirring them. By way of example, the gum kettle may be a hot-water jacketed, stainless-steel gum mixer, equipped with sigma tangential blades rotating at about 9 to about 12 rpm with about a 1:2 rotating ratio. When the molten gum base is brought to a temperature of about 50 to about 55° C., the heat can be turned off, and a sweetener, such as corn syrup, hydrogenated starch hydrolysate (HSH), or a combination thereof, at about room temperature, may be added in the desired amount to the molten gum base. The gum base and sweetener mixture preferably mixed until the sweetener is fully dispersed in the base. When the mixture is substantially homogeneous, an additional sweetener, such as sucrose, isomalt, sorbitol, xylitol, or a combination thereof, which may be in a powder form, are added and mixed until fully dispersed in the gum base and sweetener mixture. While the additional sweetener is being added, the *Heliopsis longipes* root extract, which may also be in a powder form, is also added until all of the additional sweetener and the extract are added, and the mixing is continued. Other ingredients, such as colorings or flavorings, are then added and mixed into the mixture until they are fully dispersed therein. Typically, after an ingredient is added, the mixture is stirred for about 5 minutes and the kettle is scraped before the addition of another ingredient. When the extract component is added, it may be desirable to extend the stirring time to about 10 minutes to provide good dispersion. The resulting gummy mass is discharged from the kettle, allowed to cool to a temperature of about 35 to about 40° C., and processed using any conventional gum-forming means methods to form a desired shape, such as pillows.

The liquid center of the hybrid composition may be prepared by adding all of its ingredients, such as the *Heliopsis longipes* root extract, glycerin, corn syrup, HSH, sucrose, natural gums, thickening agents, water, sweeteners, colors and flavorings, into a suitable mixer. By way of example, the mixer may be a stainless steel mixer, equipped with high-sheer agitation to facilitate the dissolution and dispersion of the ingredients. When the liquid center is substantially homogeneous, it may be injected into the gum base to form liquid-centered gum shells. Preferably, the resulting hybrid composition is substantially uniform in size, weight, and extract dosage, such as within a range of plus or minus 10%, so that acceptably uniform or predictable outcomes may be obtained.

Compositions E and F are examples of solid gums that may be used alone, or in hybrid compositions, such as those just described, that are delivered to the oral cavity as liquid-centered gum shells. In Tables 3 and 4, respectively, each of the components of Composition E and Composition F are listed, in a preferred order of addition, along with the approximate amount of each component in grams and weight percent (%) relative to the overall composition. In Tables 3a and 4a, respectively, the active blends used in Compositions E and F are detailed.

TABLE 3

Solid Gum Composition E

| Component | Weight Percent (%) | Order of Addition |
|---|---|---|
| G.B. Valentia T Cafosa | 28.00 | 1 |
| Polysorb Roquette 1000 | 16.63 | 2 |
| Acesulfame K | 0.25 | 3 |
| Glycerine - 249.90 | 0.50 | 4 |
| Sorbitol P60W Roque. | 47.08 | 5&9* |
| Mannitol 35 Roque. | 2.00 | 6 |
| Active Blend: *Heliopsis Longipes* Root Extract (on Syloid 244 at (2:1)) | 3.00 | 7 |
| Pepp SD triple dist. Flav. | 2.00 | 8 |
| Pepp Nat Mint Sec. Can | 0.80 | 10 |
| Titanium Dioxide USP | 0.00 | |
| All Components | 100.00 | |

*This component is added as the fifth component in half of the shown amount and as the ninth component in the remaining half of the shown amount.

TABLE 3a

Active Blend for Solid Gum Composition E

| Component | Parts | Basis | Weight %, Wet Basis | Weight %, Dry Basis |
|---|---|---|---|---|
| *Heliopsis Longipes* Root Extract | 2 | wet | 66.67 | 4.03 |
| Syloid 244 (silica gel) | 1 | dry | 33.33 | 95.97 |
| All Components | 3 | | 100.00 | 100.00 |

TABLE 4

Solid Gum Composition F

| Component | Weight Percent (%) | Order of Addition |
|---|---|---|
| G.B. Valentia T Cafosa | 50.00 | 1 |
| Active Blend: | | |
| *Heliopsis Longipes* Root Extract (on Syloid 244 at (50/50)) | 3.00 | 2 |
| Glycerine - 249.00 | 1.00 | 2 |
| Acesulfame K | 0.25 | 2 |
| Polysorb Roquette 1000 | 16.25 | 3 |
| Titanium Dioxide UPS | 0.50 | 3 |
| Sorbitol P60W Roque. | 23.95 | 4 |
| Pepp.SD triple dist. Flav. | 2.50 | 5 |
| Pepp Nat Mint Mint | 0.80 | 5 |
| Mannitol 35 Roque. | 2.00 | 6 |
| All Components | 100.00 | |

TABLE 4a

Active Blend for Solid Gum Composition F

| Component | Parts | Basis | Weight %, Wet Basis | Weight %, Dry Basis |
|---|---|---|---|---|
| *Heliopsis Longipes* Root Extract | 2 | wet | 66.67 | 3.85 |
| Syloid 244 (silica gel) | 1 | dry | 33.33 | 96.15 |
| All Components | 3 | | 100.00 | 100.00 |

Compositions E and F are prepared in much the same manner as the solid gum portion of the above-described hybrid composition. That is, generally, the gum base is heated in the gum kettle until molten, whereupon the heat is turned off and the remaining ingredients are added in the order shown in Tables 3 and 4 (where 1 designates the gum base; 2, 3, etc. designate the first, second, etc. ingredients added thereafter; and ingredients having the same number are added at substantially the same time). Typically, after an ingredient or group of ingredients is added, the mixture is stirred for about 5 minutes and the kettle is scraped before the addition of another ingredient or group of ingredients. When the active blend including the extract component is added, whether by itself (Composition E) or with other ingredients (Composition F), the stirring time is extended to about 10 minutes to provide good dispersion. When all of the ingredients have been added and the stirring has been completed, the solid gum is discharged from the kettle, allowed to cool to from about 35 to about 400° C., and formed into pillows or other shapes of a desirable size. While Compositions E and F may be prepared as described above, following the orders of addition described above, any other suitable preparation means or method may be used.

Compositions E and F were easily prepared and processed, and were shown to be efficacious in stimulating salivation in humans. That is, the compositions were prepared and administered to human test subjects after their baseline levels of salivation over a half-hour were determined. Baseline salivation levels were determined by having the test subjects collect their saliva in a beaker over the half-hour and then measuring the amount of saliva collected per minute. Upon administration of the composition, the test subjects' level of salivation were determined by the same method and compared to the baseline level of salivation. In all cases, an increase in salivation was observed.

In summary, extensive open label studies have been conducted of an extract of *Heliopsis longipes* made into gums, candies and liquid sprays demonstrating its effectiveness in stimulating salivation, and causing local anesthesia to the tongue, lips, gums and throat; and a variety of desirable sensations such as tingling, moistness, and a soothing quality to the tissues of the oropharynx.

According to yet another embodiment of the invention, the composition may be prepared as a tablet. By way of example, the *Heliopsis longipes* root extract component may be a fluid extract that is added to the oral carrier and any other ingredients, whereupon the composition is formulated as a tablet using any conventional means or method. The resultant tablet, including an aliquot of the extract sufficient to promote oral hygiene, may be of any desirable flavor, color, or shape.

Compositions G and H are examples of sugar-free, peppermint-flavored tablets, that are particularly useful in treating dry mouth. In Table 5, each of the components of Compositions G and H are listed along with the approximate amount of each component in weight percent (%) relative to the overall composition.

TABLE 5

Tablet Compositions G and H

| | Component | Composition G Weight Percent (%) | Composition H Weight Percent (%) |
|---|---|---|---|
| 1. | Sorbitol Powder Neosorb 6 | 97.60 | 96.55 |
| 2. | *Heliopsis Longipes* Root Extract | 1.00 | 2.00 |
| 3. | Peppermint SD BBA#21601 | 0.40 | 0.45 |
| 4. | Magnesium Stearate | 1.00 | 1.00 |
| | All Components | 100.00 | 100.00 |

The composition of the present invention, in any of the forms described herein, provides a vehicle for delivery of a dose of the *Heliopsis longipes* root extract that improves or maintains oral hygiene. A particularly preferred form of the composition is a liquid-filled solid gum shell, that provides a substantially immediate improvement in oral hygiene via salivary stimulation by the active extract of the liquid component, as well as a prolonged improvement in oral hygiene via continued salivary stimulation by the continued release of the active extract of the solid component. In this particular embodiment, the composition offers a sustained or prolonged oral delivery vehicle for the *Heliopsis longipes* root extract that provides oral hygiene benefits, such as salivary stimulation and antibiotic activity, and in particular, alleviation of dry mouth.

While the inventive composition has been described in terms of some preferred embodiments, and some preferred forms, the composition may be delivered in a variety of forms, such as lozenge and liquid spray forms, using a variety of extract concentrations, suitable for individuals or for a group of individuals. For example, the composition may be prepared in a particular form, such as any form not requiring chewing, for individuals who are edentulous or have difficulty chewing, or for individuals who may prefer such forms. For ease of use, a product or kit including a container for the inventive composition and instructions describing the use of the composition in treating any of the conditions described here in may be provided.

A variety of safety tests have been undertaken, establishing that the LD50 for the extract in use is greater than 5 gms/kg in rats; and obtaining a negative a\Ames test for mutagenicity.

A particular advantage of the inventive compositions is that they employ an extract of the *Heliopsis longipes* root, and thus, use a very small amount of the plant itself. This is especially important because the plant is believed to grow in a narrow geographic region, and thus, could be endangered by overly aggressive harvesting.

Although various aspects and features of the present invention have been described with respect to the preferred embodiments thereof, it will be understood that the invention is entitled to protection within the full scope of the appended claims.

I claim:

1. An herbal composition for oral administration comprising an extract of *Heliopsis longipes* root in an amount of about 0.01%–10% by weight of said composition in combination with an oral carrier, said composition being in a form selected from the group consisting of a powder, a gel, a paste, a tablet, a capsule, a chewable gum, a lozenge, an aerosol, and a liquid containing at least one flavoring agent;

wherein said composition provides an amount of about 0.5 mg/ml–1000 mg/ml of said extract per effective dosage.

2. The herbal composition according to claim 1 comprising about 1%–2% by weight of said *Heliopsis longipes* root extract and being in the form of a liquid comprising:

about 48% by weight distilled water;

about 20% by weight glycerine;

about 30% by weight sorbitol powder;

about 0.1% by weight potassium sorbate;

about 0.1% by weight sodium benzoate; and about 0.2% by weight citric acid powder.

3. The herbal composition according to claim 1 comprising about 1%–2% by weight of said *Heliopsis longipes* root extract and being in the form of a liquid comprising:

about 11% by weight distilled water;

about 11% by weight glycerine;

about 76% by weight sorbitol solution; and about 0.3%–0.5% by weight peppermint flavor.

4. The herbal composition according to claim 1 comprising about 3% by weight of said *Heliopsis longipes* root extract and being in the form of a gum including:

about 28% by weight gum base;

about 17% by weight polysorbate;

about 0.25% by weight acesulfame K;

about 0.5% by weight glycerine;

about 47% by weight sorbitol;

about 2% by weight mannitol; and about 3% by weight peppermint flavoring.

5. The herbal composition according to claim 1 comprising about 3% by weight of said *Heliopsis longipes* root extract and being in the form of a gum including:

about 50% by weight gum base;

about 16% by weight polysorbate;

about 0.25% by weight acesulfame K;

about 1.0% by weight glycerine;

about 24.00% by weight sorbitol;

about 2% by weight mannitol; and about 3% by weight peppermint flavoring.

6. The herbal composition according to claim 1 comprising about 1–2% by weight of said *Heliopsis longipes* root extract and being in the form of a tablet comprising:

about 97%–98% by weight sorbitol powder;

about 0.4%–0.5% by weight peppermint flavoring; and about 1.0% by weight magnesium stearate.

* * * * *